United States Patent [19]

Onik

[11] Patent Number: 4,895,171
[45] Date of Patent: Jan. 23, 1990

[54] PATIENT ISOLATION BAG

[76] Inventor: Gary Onik, 263 Courtney Pl., Wexford, Pa. 15090

[21] Appl. No.: 174,765

[22] Filed: Mar. 29, 1988

[51] Int. Cl.⁴ ............................................. A61F 13/00
[52] U.S. Cl. .................................. 128/846; 128/864; 128/871; 128/873
[58] Field of Search ................. 128/1 R, 132 D, 134, 128/155, 849, 846, 856, 872, 869, 873, 870, 871, 873; 2/69, 69.5; 604/385; 5/81 R, 82, 413, 485; 27/28

[56] References Cited

U.S. PATENT DOCUMENTS

| | | | |
|---|---|---|---|
| 1,929,263 | 10/1933 | Sork | 2/69.5 |
| 2,581,357 | 1/1952 | Burstein | 5/413 |
| 2,948,278 | 8/1960 | Topa | 128/134 |
| 3,828,784 | 8/1974 | Zoephel | 604/385 |
| 3,986,505 | 10/1976 | Power | 5/82 R |
| 4,367,728 | 1/1983 | Mutke | 128/132 R |
| 4,559,949 | 12/1985 | Levine | 128/155 |
| 4,574,397 | 3/1986 | Dennard | 2/69.5 |
| 4,616,365 | 10/1986 | Lyons | 2/69.5 |
| 4,623,342 | 11/1986 | Ito et al. | 604/38 S |
| 4,769,023 | 9/1988 | Goebel | 604/385.1 |
| 4,781,713 | 11/1988 | Welch | 604/385.1 |

Primary Examiner—Robert A. Hafer
Assistant Examiner—Michael Brown
Attorney, Agent, or Firm—Webb, Burden Ziesenheim & Webb

[57] ABSTRACT

A disposable, full-body sheath including padded areas, a body cavity, a body-receiving aperture having a face-encircling portion, areas that have sections of transparent surgical drape and fastening means. The disposable, full-body sheath provides a patient isolation bag for short-term substantial encapsulation of a patient during transport, diagnostic scanning, etc.

12 Claims, 1 Drawing Sheet

U.S. Patent  Jan. 23, 1990  4,895,171
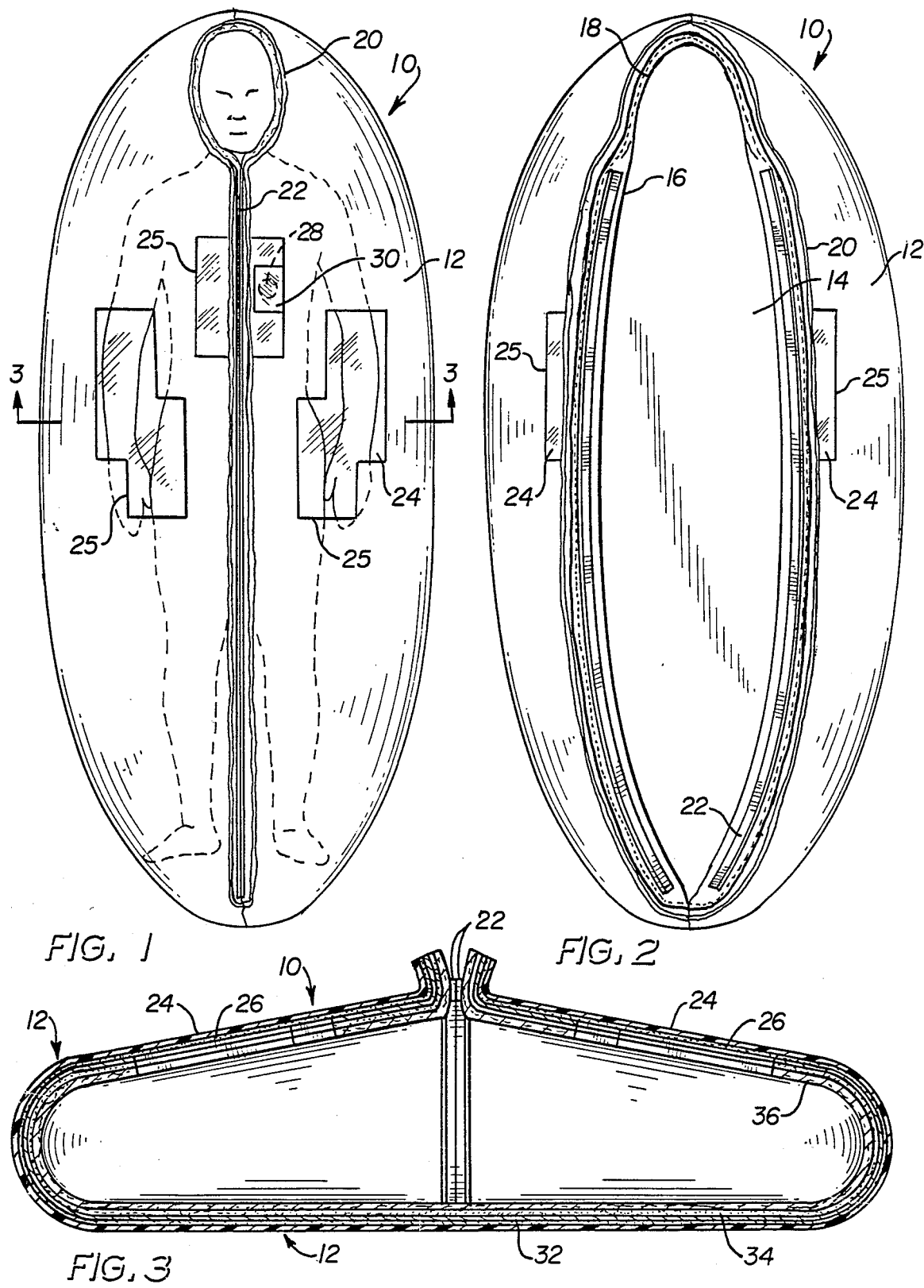

PATIENT ISOLATION BAG

FIELD OF THE INVENTION

The present invention relates to a patient isolation bag for substantial encapsulation of a patient during diagnostic scanning procedures, transport, etc.

INTRODUCTION

Safe and effective patient transport in the hospital, or other health care environment, has become a widespread institutional concern. Patient transport requirements are increasing not only as hospitals grow in size but also as technologies such as the various noninvasive diagnostic scanning techniques burgeon. With respect to the latter, the advent of additional stationary equipment mandates increased patient transport, inasmuch as equipment transport to the patient is impossible. Also, as hospital personnel begin to take increasingly more elaborate precautions against Hepatitis-B, AIDS and other threatening diseases, transport of patients having open wounds of any kind has become a renewed concern. Finally, increasing hospital costs now require that equipment as well as personnel be protected from patient contamination, as increasing labor and materials costs have made traditional sterilization protocols for such equipment inordinately expensive. A need exists, therefore, for a means for protecting equipment and transport personnel alike from patient contamination, which means neither interferes with diagnosis or transport nor compromises ongoing care of the patient.

SUMMARY OF THE INVENTION

In order to meet this need, the present invention is a patient isolation bag, for short-term encapsulation of all but the face of a patient, which bag is at least oneway outward body-fluid impermeable except where and unless breached. More particularly, the present patient isolation bag comprises a disposable, full-body sheath including padded areas, a body cavity, a body-receiving aperture, means for leaving the patient's face exposed and fastener means. Additional optional features include areas comprising sections of transparent surgical drape, having optional covered surgical drape apertures, fastener strips, an elastic member surrounding the body-receiving aperture, and a high strength reinforcement layer. The patient isolation bag therefore allows short-term substantial quarantine of a patient, which substantial quarantine can be enhanced with concurrent use of a conventional disposable hospital face mask, during patient transport or diagnostic scanning. The patient isolation bag is designed to have generous dimensions, and as a result it is large enough both for inverted placement on a gurney--for easy patient placement--and to permit even large or tall patients to assume the various required positions for testing, including arms-overhead, etc.

BRIEF DESCRIPTION OF THE DRAWINGS

Fig. 1 is a plan view of the preferred embodiment of the present invention;

FIG. 2 is a plan view of the preferred embodiment of FIG. 1 with the patient removed; and FIG. 3 is a section taken along lines 3—3 of FIG. 1.

DETAILED DESCRIPTION OF THE INVENTION

The present invention may be more particularly understood with reference to the accompanying Figures.

With reference first to FIG. 1, the patient isolation bag 10 is shown in position surrounding all but the face of a patient. The face encircling portion 18 of the body-receiving aperture may expose substantially all of the facial structures included in the ventral portions of the cranium, as illustrated, or may additionally cover a portion of the ventral cranium so as to expose primarily the maxillofacial area and the eyes. In no event should the eyes and/or maxillofacial area be covered or obscured from view, not only to maintain the patient airway but also to allow monitoring of the patient's skin color, eye reflexes, etc., as necessary.

Except for the exposed face, therefore, the patient isolation bag 10 of FIG. 1 covers and encapsulates the entire patient. The patient isolation bag 10 consists predominantly of padded areas 12, although limited areas 25 of transparent surgical drape material 24 are provided in strategic locations, to allow patient access. The areas 25 of transparent surgical drape material 24 are backed with the adhesive layer generally used in the art, so that they may be actively adhered to the skin of the patient and procedures may be performed therethrough. For example, injections, intravenous placement and other procedures may be effected directly through the surgical drape material. Two of the three areas 25 of transparent surgical drape material 24 are shown away from and on either side of the midline of the patient. This design reflects the ability of the patient care provider to access the femoral artery, the trachea, and other midline or near-midline anatomic structures by first opening a small breach in the fastener strips 22. The fastener strips 22, as illustrated, secure the patient isolation bag 10 into a single capsule-like structure after the patient is in place. Because the fastener strips 22 are ordinarily removably adhesive fastener strips such as are found in disposable diapers, these minor breaches or openings in the fastener strips are easily effected. Moreover, the minor breach for access to the patient may be readily reversed by resealing of the fastener strips 22; either to their original mated position or adjacent and surrounding any tubes, etc., remaining.

It is to be noted that although the areas 25 of transparent surgical drape material 24 have been shown in particular position in the preferred embodiment shown in FIG. 1, these transparent surgical drape sections may be placed at any anatomic position desired. In addition, even the areas 25 as shown can be easily applied (i.e., adhered) to a different position on a patient. For example, either of the two lowermost areas 25 could be repositioned slightly on the patient to allow access to the femoral artery. The transparent surgical drape material 24 may of course be provided with a release layer on the inside of any adhesive backing present, so that the surgical drape areas may be adhered selectively to the patient, only when needed.

One of the areas 25 of transparent surgical drape material 24, consisting of two half-rectangles positioned side-by-side, includes the surgical drape aperture 28, having the transparent surgical drape aperture cover 30 thereover. The aperture 28 is merely a hole, and the transparent surgical drape aperture cover 30 is simply a second layer of the same surgical drape material 24.

These structures allow for convenient access in the area of the thorax, for use when necessary.

The patient isolation bag of FIG. 1 may be shaped into its characteristic single-expanse, elongated (flat) oval shape by means known in the art, including heat pressing, molding, sealed end seams, sealed darts and the like. Alternatively, the patient isolation bag 10 may be formed of a large rectangle of the bag material, with elastic at all the edges thereof, to form a "gathered" structure. The shaped configuration as shown is preferred, however, to avoid unwanted bulk around the patient and to maximize materials economy.

FIG. 2 illustrates the patient isolation bag 10 of the present invention with the patient removed. The body receiving aperture 16 of the patient isolation bag is illustrated, along with the body cavity 14 which receives the patient. An elastic band 20 encircles the body receiving aperture 16; the elasticity of this elastic band 20 allows the patient isolation bag 10 to be inverted over a gurney or similar structure. The cooperating fastener strips 22 can be seen more readily in FIG. 2 than in FIG. 1. These fastener strips 22 are typical of the removably adhesive fastener strips employed in disposable diaper structures, and consist generally of a first strip bearing a pressure-sensitive adhesive and a second strip bearing a smooth polymer surface, releasably adherent to the pressure-sensitive adhesive layer on the first strip. The seal between the two surfaces of the two strips preferably creates a one-way outward body-fluid impermeable seal.

FIG. 3 is a section taken along lines 3-3 of FIG. 1. FIG. 3 illustrates the various layers of the embodiment of the invention shown in FIG. 1. More particularly, FIG. 3 illustrates the innermost pad layer 36 of the patient isolation bag 10, next to which, in order, is an adhesive layer 34, a reinforcement layer 32, a transparent surgical drape adhesive layer 26 and the transparent surgical drape material 24. Because FIG. 1 shows the transparent surgical drape material 24 adhered to the patient, the section of FIG. 3 necessarily does not show a release liner backing the transparent surgical drape adhesive 26, but those skilled in the art will understand that such a release liner can be readily adapted to cover the transparent surgical drape adhesive 26 until the patient isolation bag 10 is positioned on the patient.

In the preferred embodiment of the invention as shown in the Figures, the transparent surgical drape adhesive 26 extends throughout the entire laminate, as does the transparent surgical drape material 24. For economical construction, therefore, the entire outer surface of the patient isolation bag consists of transparent surgical drape material 24 backed by transparent surgical drape adhesive 26, with the areas 25 of transparent surgical drape material 24 being defined by the absence of any of the other layers. Preparation of laminates having this configuration not only maximizes materials and manufacturing economy but also provides for an outer layer to the patient isolation bag 10 which maximizes both comfort and maintenance of sanitary conditions. Any of the surgical drape materials commonly used in surgical drape products may be used in the present invention, so long as the material exhibits at least oneway outward body-fluid and microorganism impermeability unless breached. The material, accordingly, may be moisture-vapor permeable as long as it is microorganism impermeable. The various urethanes and polyurethanes typically employed in surgical drapes known in the art are thus suitable for use.

The reinforcement layer 32 may be prepared of strong materials including fabrics and textiles, or may include strong polymeric materials which are thin, lightweight and inexpensive such as, for example, Tyvek ®, spunbonded olefin sheet available from E.I. duPont de Nemours. The reinforcement layer 32 and the accompanying adhesive layer 34 are, of course, optional, but are present in the preferred embodiment of the patient isolation bag 10. The reinforcement layer enables patient shifting by grasping and pulling the bag material itself; the reinforcement layer 32 prevents tearing.

Absorbent pad materials for use in the present invention may include virtually any padding materials, particularly those suitable for use in the manufacture of disposable diapers, although all pad materials are appropriate except those which exhibit allergic or toxic properties to the skin. Generally, pad materials consist of cellulosics, other natural fibers, synthetics, or blends of the above, in mat, batt or foam layers.

Although the present invention has been described with respect to specific materials and structures, widespread changes may be made to the preferred embodiment illustrated in the Figures. For example, the patient isolation bag 10 may be constructed in its entirety of transparent surgical drape and associated adhesive, with the padded areas being adhered to the transparent surgical drape adhesive by means of an integral release liner on one side of the pad. In use, the patient is positioned within the patient isolation bag, and the desired sections of the pad are simply removed at desired anatomic positions. The pad may be perforated in a quilt-like configuration to facilitate this. The elastic band 20 which encircles the body-receiving aperture 16 of the preferred embodiment may be eliminated entirely or provided in sections, as needed. The elastic band 20 may be manufactured of any stretchable-recoverable material. The fastener strips 22 may be provided in segments instead of two long strips as shown, or similar fastener means may be provided to secure the patient isolation bag 10 around the patient.

Although the invention has been described particularly above, the invention is to be limited only insofar as is set forth in the accompanying claims.

I claim:

1. A patient isolation bag, comprising:
   a layer of surgical drape material;
   a reinforcement layer;
   a layer of adhesive attaching said surgical drape material to said reinforcement layer;
   a layer of absorbent padded areas; and
   a layer of adhesive attaching said layer of absorbent padded areas to said reinforcement layer;
   wherein each of said layer is included within a laminate and further wherein said laminate forms a sheath which is adapted to encircle a patient's body.

2. The patient isolation bag according to claim 1, wherein said laminate further comprising a single expanse having edges which define an aperture in the patient isolation bag, said aperture having a length approximately equal to the height of a patient for which the patient isolation bag is sized.

3. The patient isolation bag according to claim 2, wherein fastener strips append said laminate adjacent said edges which define an aperture.

4. The patient isolation bag according to claim 3, wherein said fastener strips further comprise two fastener strips, one of which appends said laminate on either side of said aperture.

5. The patient isolation bag according to claim 4, wherein said two fastener strips further comprise one pressure-sensitive adhesive first strip and on releasable mating second strip.

6. The patient isolation bag according to claim 5, wherein said aperture includes a face-encircling portion.

7. The patient isolation bag according to claim 6, wherein a stretchable-recoverable material is positioned in an at least substantially continuous band encircling said edges which define an aperture.

8. The patient isolation bag according to claim 7, wherein said two fastener strips are positioned between said stretchable-recoverable material and said edges which define an aperture.

9. The patient isolation bag according to claim 8, wherein said layer providing absorbent padded areas is constructed of materials suitable for contact with human skin.

10. The patient isolation bag according to claim 9, wherein said absorbent padded areas are perforated in a quilt-like pattern, whereby individual sections of said absorbent padded areas may be removed as necessary.

11. The patient isolation bag according to claim 10, wherein at least one section of said laminate consists of said layer of surgical drape material backed by said layer of pressure sensitive adhesive.

12. The patient isolation bag according to claim 1, wherein each layer of adhesive further comprises a layer of pressure sensitive adhesive.

* * * * *